United States Patent [19]

Mehra et al.

[11] Patent Number: 4,883,515
[45] Date of Patent: Nov. 28, 1989

[54] PROCESSING HYDROCARBON GASES WITH SELECTED PHYSICAL SOLVENTS

[75] Inventors: Yuv R. Mehra, The Woodlands; Freylon B. Coffey, Austin, both of Tex.

[73] Assignee: Advanced Extraction Technologies, Inc., Houston, Tex.

[21] Appl. No.: 102,350

[22] Filed: Sep. 29, 1987
(Under 37 CFR 1.47)

Related U.S. Application Data

[63] Continuation-in-part of Ser. No. 100,242, Sep. 23, 1987, Pat. No. 4,832,718, which is a continuation-in-part of Ser. No. 74,226, Jul. 16, 1987, which is a continuation-in-part of Ser. No. 24,561, Mar. 11, 1987, Pat. No. 4,740,222, which is a continuation-in-part of Ser. No. 854,383, Apr. 21, 1986, Pat. No. 4,743,282, which is a continuation-in-part of Ser. No. 828,996, Feb. 13, 1986, Pat. No. 4,696,688, which is a continuation-in-part of Ser. No. 828,988, Feb. 13, 1986, Pat. No. 4,680,042, which is a continuation-in-part of Ser. No. 808,463, Dec. 13, 1985, Pat. No. 4,692,179, which is a continuation-in-part of Ser. No. 784,566, Oct. 4, 1985, Pat. No. 4,817,038, which is a continuation-in-part of Ser. No. 759,327, Jul. 26, 1985, Pat. No. 4,623,371, which is a continuation-in-part of Ser. No. 758,351, Jul. 24, 1985, Pat. No. 4,601,738, which is a continuation-in-part of Ser. No. 637,210, Aug. 3, 1984, Pat. No. 4,578,094, which is a continuation-in-part of Ser. No. 532,005, Sep. 14, 1983, Pat. No. 4,526,594, which is a continuation-in-part of Ser. No. 507,564, Jun. 24, 1983, Pat. No. 4,511,381, which is a continuation-in-part of Ser. No. 374,270, May 3, 1982, Pat. No. 4,421,535.

[51] Int. Cl.$^4$ .............................................. F25J 3/00
[52] U.S. Cl. .......................................... 62/17; 55/68; 62/20
[58] Field of Search ................ 62/9, 11, 17, 18, 20; 55/68, 69, 74, 75

[56] References Cited

U.S. PATENT DOCUMENTS

Re. 23,768  1/1954  Cope et al. ................. 196/14.41
1,220,651  3/1917  Linderborg et al. .
1,768,521  6/1930  Ayres, Jr. .

(List continued on next page.)

OTHER PUBLICATIONS

"High CO$_2$–High H$_2$S Removal with Selexol Solvent", by John W. Sweny, 59th Annual GPA Convention, Mar. 17–19, 1980, Houston, Texas.

"Gas Absorption", as Chapter 8 in *Mass Transfer Operations*, by Treybal, McGraw-Hill Book Company, Second Edition, 1968, pp. 221–226 and 393–395.

"Humble's Avery Island Plant: High Safety at Low Cost", by J. J. Weatherby, *Hydrocarbon Processing & Petroleum Refiner*, Apr. 1962, vol. 41, No. 4, pp. 113–116.

"Absorption under Liquefied Petroleum Gas", in vol. 14 of *Kirk–Othmer Encyclopedia of Chemical Technology*, Third Edition, 1980, pp. 383–388.

*Gas Processors Report, Texas Coast*, Spears Consulting Group, P.O. Box 33002, Tulsa, OK 74153, Oct. 14, 1985, pp. 1, 7, and 8.

*Primary Examiner*—Ronald C. Capossela
*Attorney, Agent, or Firm*—Depaoli & O'Brien

[57] ABSTRACT

A continuous process is disclosed for separating components of a hydrocarbon gas stream which are selected from the group consisting of methane, ethane, higher saturated hydrocarbons, and mixtures thereof by countercurrently contacting the hydrocarbon gas stream with a physical solvent selected from the group consisting of:

(1) paraffinic solvents having molecular weights ranging from 75 to 140 and UOP characterization factors ranging from 12.0 to 13.5, these factors being independent of the aromatic content of the paraffinic solvents, (2) naphthenic solvents having molecular weights ranging from 75 to 130 and UOP characterization factors ranging from 10.5 to 12.0, these factors being independent of the aromatic content of the naphthenic solvents, and (3) benzene and toluene, to produce an overhead stream which is rich in methane and a rich solvent bottoms stream and then recovering the lean physical solvent and a C$_2$+ hydrocarbons product from the rich solvent bottoms stream and recycling the recovered solvent stream to the contacting step.

5 Claims, 3 Drawing Sheets

4,883,515

U.S. PATENT DOCUMENTS

| | | | |
|---|---|---|---|
| 1,929,841 | 10/1933 | Fitch et al. | 62/179 |
| 1,953,043 | 3/1934 | Cole, Jr. et al. | 196/8 |
| 2,241,717 | 5/1941 | Robinson et al. | 196/10 |
| 2,290,957 | 7/1942 | Hachmuth | 196/8 |
| 2,320,127 | 5/1943 | Hachmuth | 260/683.4 |
| 2,355,167 | 8/1944 | Keith | 62/175.5 |
| 2,428,521 | 10/1947 | Latchum, Jr. | 196/8 |
| 2,451,136 | 10/1948 | Wenzke | 183/115 |
| 2,620,895 | 12/1952 | Turner | 183/120 |
| 2,782,141 | 2/1957 | King | 196/8 |
| 2,849,371 | 8/1958 | Gilmore | 196/8 |
| 2,868,326 | 1/1959 | Gilmore | 55/73 X |
| 2,938,865 | 5/1960 | Moyer | 208/341 |
| 3,210,949 | 10/1965 | Wienecke | 62/17 |
| 3,214,890 | 11/1965 | Sterrett | 55/40 |
| 3,236,029 | 2/1966 | Afdahl et al. | 55/44 |
| 3,287,262 | 11/1966 | Jones | 208/341 |
| 3,907,669 | 9/1975 | Ward | 208/341 |
| 4,009,097 | 2/1977 | Ward | 208/342 |
| 4,150,962 | 4/1979 | Colton | 62/17 |
| 4,368,058 | 1/1983 | Crowley et al. | 55/21 |
| 4,526,594 | 7/1985 | Mehra | 62/17 |
| 4,556,404 | 12/1985 | Shenoy et al. | 62/17 |
| 4,657,571 | 4/1987 | Gazzi | 62/17 |

PROCESSING HYDROCARBON GASES WITH SELECTED PHYSICAL SOLVENTS

RELATED APPLICATIONS

This is a continuation-in-part of a copending application Ser. No. 100,242 of Yuv R. Mehra, entitled "Processing Nitrogen-Rich, Hydrogen-Rich, and Olefin-Rich Gases with Physical Solvents", filed Sept. 23, 1987 now U.S. Pat. No. 4,832,718, which is a continuation-in-part of a copending application Ser. No. 074,226, filed July 16, 1987, which is a continuation-in-part of copending application Ser. No. 024,561, filed Mar. 11, 1987 now U.S. Pat. No. 4,740,222, which is a continuation-in-part of co-pending application Ser. No. 854,383, filed Apr. 21, 1986 now U.S. Pat. No. 4,743,282, which is a continuation-in-part of co-pending application Ser. No. 828,996, filed Feb. 13, 1986, issuing as U.S. Pat. No. 4,696,688, and of application Ser. No. 828,988, filed Feb. 13, 1986 and now U.S. Pat. No. 4,680,042, which are continuation-in-part of application Ser. No. 808,463, filed Dec. 13, 1985, now U.S. Pat. No. 4,692,179, which is a continuation-in-part of application Ser. No. 784,566, filed Oct. 4, 1985, now U.S. Pat. No. 4,817,038, which is a continuation-in-part of application Ser. No. 759,327, filed July 26, 1985, now U.S. Pat. No. 4,623,371, which is a continuation-in-part of application Ser. No. 758,351, filed July 24, 1985, now U.S. Pat. No. 4,601,738, which is a continuation-in-part of application Ser. No. 637,210, filed Aug. 3, 1984, now U.S. Pat. No. 4,578,094, which is a continuation-in-part of application Ser. No. 532,005, filed Sept. 14, 1983, now U.S. Pat. No. 4,526,594, which is a continuation-in-part of application Ser. No. 507,564, filed June 24, 1983, now U.S. Pat. No. 4,511,381, which is a continuation-in-part of application Ser. No. 374,270, filed May 3, 1982, now U.S. Pat. No. 4,421,535.

BACKGROUND OF THE INVENTION

1. Field of the Invention

This invention relates to solvent extraction of a natural gas stream with selected physical solvents to produce $C_2+$ hydrocarbon products.

2. Review of the Prior Art

U.S. Pat. No. 2,782,141 describes a process for dehydrating a wet natural gas with ethylene glycol, front end cooling to remove all $C_4+$ components and part of the propane, absorption with a refrigerated lean oil at 450 psig, flashing the rich oil to a pressure of about 60 psig, and dehydrating and then refrigerating the lean gas from the absorption zone to remove $C_5+$ condensate utilized from the absorber oil which is about 98.5% hexane and heavier. The process is an improvement on conventional processes using an absorption oil which is stated to be a moderately high boiling hydrocarbon liquid having a molecular weight range of 150–300 and a normal boiling range of 350°–500° F., this oil being passed through the absorption zone at rates of about 10–100 gallons per thousand cubic feet of feed gas. Because this feed rate is relatively high, it invariably causes lean gas product contamination and consequently requires periodic decontamination in a separate distillation operation. The products of this process are a dry gas containing methane and ethane and a liquefied product containing as high as 95% of the propane together with the $C_4+$ constituents.

U.S. Pat. No. 2,868,326 discloses a process for treating a hydrocarbon gas containing hydrogen sulfide with an absorption oil in a deethanizing absorber and in a propane absorber. The absorption oils may each be a gasoline fraction or may be a straight run oil (400° F.E.P.).

U.S. Pat. No. 2,938,865 describes an extractive distillation process for treating a hydrocarbon gas, such as a compressed, wet gas obtained as the overhead after fractionating the gas produced by catalytic cracking of a gas oil, the absorption oil having a boiling range which is close to the boiling range of the material being separated from the feed material. A suitable absorption oil for use in a deethanizing absorber is an unstabilized gasoline having an end point of about 400° F. and containing some butane.

U.S. Pat. No. 3,236,029 relates to recovery of propane from the overhead gas stream of a deethanizer still which uses a lean absorption oil, such as a mineral seal oil, without need for use of a propane-ethane fractionating column. The rich oil from the absorber is flashed to remove methane, heated, and fed to the upper portion of the stripping section of an extractive distillation column used as the deethanizing absorber. Absorption oil from a stripping still is fed to the top of the absorber section of the same column.

U.S. Pat. No. 3,287,262 describes a process for treating raw or wet natural gas to recover therefrom gasoline-boiling range hydrocarbons, particularly $C_3$-$C_6$ hydrocarbons. The natural gas is fed to the bottom of an absorber which also receives at its top a presaturated lean oil at 6° F. The rich oil from this absorber is fed at $-20°$ F. to the midsection of an extractive distillation column used for deethanizing. This column has a pre-saturator at its top above its upper section, in which the ethane is absorbed in the lean oil as the gases rise from the lower section, thereby preparing a feed for the absorber column. A lean absorption oil is fed to the top of the pre-saturator for this purpose. A separate stream of lean oil is also fed to the top of the upper section, beneath the pre-saturator.

U.S. Pat. No. 3,907,669 provides lower energy consumption in a process for the separation and recovery of desired liquid and vapor constituents from a feed stream containing them. The feed stream is contacted with the lean absorption oil in an absorption column, and the resultant rich oil is passed to a stripping column having a reboiler and then to a fractionation column. A portion of the stripped oil is withdrawn from the stripping column and a balance of the absorption oil from the fractionation column. Energy consumption is decreased because the portion of absorption oil withdrawn from the stripping column does not pass through the fractionation column.

U.S. Pat. No. 4,009,097 relates to a process for recovery of selected hydrocarbon liquid and vapor constituents from a feed stream by countercurrent absorption with primary and secondary lean oils in an absorption zone, stripping the rich oil from the bottom of the zone, passing the stripped oil to a fractionation zone, mixing the stripped vapor with the feed stream, cooling this mixture to cause partial condensation thereof, separating the cooled mixture into liquid and vapor phases, introducing the vapor phase into the bottom of the absorption zone, and introducing the liquid phase into the absorption zone at a higher point, introducing the mixture of vapor and feed into the absorption zone, returning a portion of the fractionation bottoms to the absorption zone as the secondary lean oil, and returning a portion of the stripped oil to the absorption zone as the primary lean oil.

U.S. Pat. No. 4,368,058 describes a process for controlling the flow of lean absorption oil to the absorption section of an absorber column by measuring the pressure drop across an absorption section of the column. A portion of a vapor is condensed and the oil thus produced is employed as the absorption oil to recover a more readily absorbed portion of the vapors and thus produce a rich oil. Flow of lean oil can be maximized, short of flooding, responsive to the measured pressure differential.

A new selective solvent process has recently been available for the extraction of hydrocarbon liquids from natural gas streams. This process, known as the Mehra Process, utilizes a preferential physical solvent for the removal and recovery of desirable hydrocarbons from a gas stream. In the presence of a selected preferential physical solvent, the relative volatility behavior of hydrocarbons is enhanced. The selected solvent also has high loading capacity for desirable hydrocarbons.

If hydrocarbons heavier than methane, such as ethane, ethylene, propane, propylene, butanes, etc., are present, they can be selectively removed from the gas stream as a combined liquids product by using the Mehra Process. The hydrocarbon component recoveries can be adjusted to any degree varying in the range of 2-98+% for methane, 2-90+% for ethane, and 2-100% for propane and heavier hydrocarbons.

In the Mehra Process, methane is generally considered to be one of the undesirable hydrocarbons which leaves the process as residual gas. However, as taught in U.S. Pat. No. 4,526,594, the residue gas can be selectively purified to become the product gas. The Mehra Process accordingly provides flexible recovery to a selected degree of only economically desirable hydrocarbons as a hydrocarbon liquids product or as a product gas.

Even though the Mehra Process was developed with the viewpoint that economical operation was essential, the superior absorbing qualities of preferential physical solvents, such as mesitylene, compared to "lean oils" were unquestioned. Such absorption oils are truly lean only between the bottom of the regenerator column and the top of the absorption column. They should accordingly be described as lean "lean oil" or rich "lean oil"; preferably, the term, "absorption oil", should be employed.

According to the "Engineering Data Book", Vol II, Sections 17-26, Tenth Edition, 1987, published by the Gas Processors Suppliers Association, 6526 East 60th Street, Tulsa, Ok. 74145, absorption is one of the oldest unit operations used in the gas processing industry. For a given gas, the fraction of each component in the gas that is absorbed by an oil is a function of the equilibrium phase relationship of the components and lean oil, the relative flow rates, and the contact stages. The phase relation is a function of pressure, temperature and the composition of the lean oil.

As components are absorbed, the temperature of the gas and oil phases increases due to heat of absorption. The heat released is proportional to the amount of gas absorbed. In many cases, side coolers are used on the absorber to limit the temperature rise and aid in absorption.

Lean oil typically has a molecular weight in the 100 to 200 range. For ambient temperature absorbers, a heavy lean oil of 180 to 200 molecular weight is normally used. For refrigerated absorbers, a lighter lean oil of 120 to 140 molecular weight is used. A lower molecular weight lean oil contains more moles per gallon, resulting in a lower circulation rate. However, a lower molecular weight lean oil will have higher vaporization losses.

The stripping column is operated at low pressures and high temperatures. Refrigerated lean oil plants normally use direct fixed heaters to vaporize a portion of the rich oil in the stripper (still) to provide the necessary stripped vapor.

In a Summary Report by Grant M. Wilson et al, entitled "K-Values in Absorber Oil-Natural Gas Systems, Experimental Study", Sept. 5, 1968, from P-V-T, Incorporated, P.O. Box 36272, Houston, Tex. 77036, for the Natural Gas Processors Association, 808 Home Federal Building, 404 South Boston, Tulsa, Ok. 74103, the results of 34 tests on two absorption oils were given, according to the following outline:

|  | Series I | Series II |
| --- | --- | --- |
| Temperature, °F. | +40, 0, −40 | +40, 0, −20, −40 |
| Pressure, Psia | 500, 1000, 1500 | 500, 1000, 1250, 1500 |
| Composition to simulate | absorber top, absorber bottom | absorber bottom |
| Absorber oil | 103 molecular weight | 130 molecular weight |

Supplemental data on the 130 molecular weight lean oil are as follows:

| FRACTIONAL DISTILLATION | |
| --- | --- |
| IBP-221° | 2.32% |
| 221-250° | 3.65% |
| 250-276° | 12.27% |
| 276-300° | 20.56% |
| 300° + | 61.20% |
| | 100.00% |

| Combined Fractional Distillation, Mass Spectrometer and Flame Ionization Chromotographic Analysis | |
| --- | --- |
| | Liquid Volume % |
| Pentane and Lighter | Trace* |
| Cyclohexane | 0.23 |
| Benzene | 0.06 |
| Hexane Paraffins | 1.20 |
| Hexane Naphthenes (5 Ring) | 0.28 |
| Hexane Naphthenes (6 Ring) | 0.44 |
| Toluene | 0.43 |
| Octane Normal and iso-Paraffins | 8.90 |
| Octane Naphthenes (5 Ring) | 1.32 |
| Octane Naphthenes (6 Ring) | 4.04 |
| Octane Alkyl Benzenes (Total) Distribution | 4.74 |
| Ethyl Benzene | 0.54 |
| Para-Xylene | 0.67 |
| Meta-Xylene | 2.35 |
| Ortho-Xylene | 1.18 |
| Nonanes Plus Normal and iso-Paraffins | 41.75 |
| Nonanes Plus Monocycloparaffins | 26.43 |
| Nonanes Plus Dicycloparaffins | 2.80 |
| Nonanes Plus Tricycloparaffins | 1.12 |
| Indanes | Trace* |
| Naphthalene | Trace* |
| Nonanes Alkyl Benzene | 4.81 |
| Decanes Alkyl Benzene | 1.40 |
| Undecanes Alkyl Benzene | 0.05 |
| | 100.00 |

*Trace denotes less than 0.01%

The 103 molecular weight lean oil had the following properties:

| Component | Analysis Mole % | Average Carbon Number of Cut | ASTM Engler Distillation Volume % Over | Temperature °F. |
|---|---|---|---|---|
| Propane | 0.0028 | 3 | I.B.P. | 186 |
| iso-Butane | 0.47 | 4 | 5 | 203 |
| n-Butane | 1.08 | 4 | 10 | 210 |
| iso-Pentane | 1.75 | 5 | 20 | 216 |
| n-Pentane | 1.35 | 5 | 30 | 220 |
| Hexanes | 3.75 | 5.92 | 40 | 224 |
| Heptanes | 21.70 | 6.98 | 50 | 226 |
| Octanes | 47.77 | 7.74 | 60 | 229 |
| Nonanes | 18.41 | 8.18 | 70 | 232 |
| Decanes | 2.75 | 9.58 | 80 | 239 |
| Undecanes Plus | 0.95 | — | 90 | 254 |
|  |  |  | 95 | 278 |
|  |  |  | E.P. | 325 |
|  |  |  | Recovery | 98.8 |
|  |  |  | Residue | 1.2 |
| PONA Analysis | % |  | Specific Gravity |  |
| Aromatics | 12.2 |  | 60° F./60° F.: |  |
| Naphthenes | 39.8 |  | 0.7405 |  |
| Paraffins | 47.5 |  | Density at 1500 psia and 75° F.: |  |
| Dicycloparaffins | 0.4 |  | 0.7398 g/cc |  |

The 130 molecular weight lean oil had the following properties:

| Component | Analysis Mole % | Average Carbon Number of Cut | ASTM Engler Distillation Volume % Over | Temperature °F. |
|---|---|---|---|---|
| Propane | 0.0061 | 3 | I.B.P. | 242 |
| iso-Butane | 0.0092 | 4 | 5 | 270 |
| n-Butane | 0.013 | 4 | 10 | 283 |
| iso-Pentane | 0.023 | 5 | 20 | 294 |
| n-Pentane | 0.017 | 5 | 30 | 300 |
| Hexanes | 0.45 | 5.92 | 40 | 306 |
| Heptanes | 2.09 | 6.91 | 50 | 312 |
| Octanes | 10.20 | 7.71 | 60 | 319 |
| Nonanes | 32.96 | 8.71 | 70 | 328 |
| Decanes | 34.00 | 9.64 | 80 | 340 |
| Undecanes Plus | 20.23 | — | 90 | 361 |
|  |  |  | 95 | 386 |
|  |  |  | E.P. | 435 |
|  |  |  | Recovery | 98.6 |
|  |  |  | Residue | 1.4 |
| PONA Analysis | % |  | Specific Gravity |  |
| Aromatics | 11.9% |  | 60° F./60° F.: |  |
| Naphthenes | 35.6 |  | 0.7703 |  |
| Paraffins | 52.2 |  |  |  |
| Olefins | 0.3 |  |  |  |
| Molecular Weight | 130 |  |  |  |

For both oils, 50% of the total area of the chromatograph was cut on a apiezon column at 320° F. All components were assumed to be paraffins in averaging calculations for the Average Carbon Number of Cut.

SUMMARY OF THE INVENTION

It has suprisingly been discovered that certain paraffinic and naphthenic solvents possess higher solubilities for hydrocarbons than the aromatic and other preferential physical solvents described in the following Yur R. Mehra U.S. Pat. Nos. 4,421,535, 4,511,381, 4,526,594, 4,578,094, 4,601,738, 4,617,038, 4,623,371, 4,692,179, 4,680,017, 4,696,688, 4,740,226, 4,743,282 and 4,832,718. These patents are hereby incorporated herein by reference.

The following application of Yuv R. Mehra is also hereby incorporated by reference: Ser. No. 07/074,226.

It is accordingly an object of this invention to provide combinations of selected solvent extraction processes for hydrocarbon gas mixtures with certain solvents selected according to novel criteria and further with selected pressure, temperature, solvent flow rate, and gas flow rate conditions in specific apparatus arrangements to produce desired recoveries of the $C_2+$ components of the gaseous mixtures under economical construction and operating conditions.

It is also an object to apply these solvent selection criteria to processes for treating natural gas to separate the $C_2+$ hydrocarbon components thereof from the methane. This invention is based upon the discovery that the paraffinic, naphthenic, and lighter aromatic solvents offer significant potential for (a) lower initial capital investment and (b) lower ongoing operating costs because it has been found that higher solubility properties outweigh outstanding selectivity properties on a cost basis. Specifically, lower selectivities can be compensated for by additional height in an extraction column, whereas lower solubilities can only be compensated for by greater column diameters and higher solvent flow rates, causing higher capital and operating costs.

These selection criteria, whether they are applicable to a mixture of compounds or to a pure compound, are the molecular weight and the UOP characterization factor for each solvent. Paraffinic solvents, naphthenic solvents, and lighter aromatic solvents have distinctive ranges for each criterion.

For the purposes of this invention, as shown in Table I, all physical solvents from the group of paraffinic and naphthenic solvents having molecular weights ranging from 75 MW to 140 MW, plus benzene and toluene among the aromatic group, are considered to be useful additional solvents for the Mehra Process. This group of paraffinic solvents is additionally defined as solvents having UOP characterization factors ranging from 12.0 to 13.5. The naphthenic solvents are defined as those having UOP characterization factors ranging from 10.5 to 12.0. Both of these definitions are independent of the solvent's aromatic contents.

When the molecular weight of each paraffinic solvent is less than 75, solubility in the solvent is at its highest, but the cost of separating the product from the solvent, as in the product column, fractionator, or regenerator, becomes prohibitive. Further, systems using solvents of molecular weight less than 75 inherently require a solvent recovery system.

TABLE I

| | | | | UOP | AVG. ASTM D-86 DISTILLATION BP TEMPERATURES, °F., AT INDICATED PERCENTAGES OF FEED DISTILLED | | | | | | | | | | | | | |
|---|---|---|---|---|---|---|---|---|---|---|---|---|---|---|---|---|---|---|
| Type | MW | S.G. | API | K | °F. | IBP | 5% | 10% | 20% | 30% | 40% | 50% | 60% | 70% | 80% | 90% | 95% | EP |
| Paraffinic | 75 | 0.6436 | 88.36 | 12.7 | 98 | 70 | 88 | 91 | 93 | 96 | 97 | 98 | 100 | 101 | 104 | 110 | 124 | 174 |
| Paraffinic | 85 | 0.6566 | 84.00 | 12.8 | 136 | 106 | 125 | 128 | 131 | 134 | 135 | 136 | 138 | 140 | 142 | 149 | 163 | 217 |
| Paraffinic | 100 | 0.6830 | 75.67 | 12.7 | 194 | 161 | 182 | 185 | 188 | 191 | 193 | 194 | 196 | 198 | 201 | 208 | 224 | 283 |
| Paraffinic | 110 | 0.6992 | 70.87 | 12.6 | 234 | 199 | 222 | 225 | 228 | 231 | 233 | 234 | 236 | 238 | 241 | 249 | 266 | 328 |
| Paraffinic | 120 | 0.7130 | 66.96 | 12.6 | 270 | 233 | 257 | 261 | 263 | 267 | 269 | 270 | 272 | 274 | 277 | 286 | 304 | 369 |
| Paraffinic | 130 | 0.7231 | 64.19 | 12.6 | 302 | 263 | 288 | 292 | 295 | 299 | 301 | 302 | 304 | 307 | 310 | 319 | 337 | 406 |
| Paraffinic | 140 | 0.7322 | 61.75 | 12.6 | 328 | 288 | 314 | 318 | 321 | 325 | 327 | 328 | 330 | 332 | 336 | 345 | 365 | 435 |
| Naphthenic | 75 | 0.7569 | 55.46 | 11.0 | 124 | 94 | 113 | 116 | 119 | 122 | 123 | 124 | 126 | 128 | 130 | 137 | 151 | 203 |
| Naphthenic | 85 | 0.7689 | 52.53 | 11.1 | 169 | 137 | 158 | 161 | 163 | 166 | 168 | 169 | 171 | 173 | 175 | 183 | 198 | 255 |
| Naphthenic | 110 | 0.7843 | 48.92 | 11.4 | 260 | 223 | 247 | 251 | 254 | 257 | 259 | 260 | 262 | 264 | 267 | 276 | 293 | 358 |
| Naphthenic | 130 | 0.7960 | 46.26 | 11.4 | 290 | 252 | 276 | 280 | 283 | 287 | 289 | 290 | 292 | 295 | 298 | 307 | 324 | 392 |
| Benzene | 78 | 0.8845 | 28.48 | 9.7 | 176 | | | | | | | | | | | | | |
| Toluene | 92 | 0.8719 | 30.79 | 10.1 | 231 | | | | | | | | | | | | | |
| Ethylbenzene | 106 | 0.8717 | 30.83 | 10.4 | 277 | | | | | | | | | | | | | |
| m-Xylene | 106 | 0.8688 | 31.37 | 10.4 | 282 | | | | | | | | | | | | | |
| Mesitylene | 120 | 0.8709 | 30.98 | 10.6 | 332 | | | | | | | | | | | | | |
| Pseudocumene | 120 | 0.8811 | 29.09 | 10.5 | 339 | | | | | | | | | | | | | |

When the molecular weight of a paraffinic solvent exceeds 140, or when the molecular weight of a naphthenic solvent exceeds 130, these solvents no longer exhibit an improvement in solubility relative to preferential physical solvents previously disclosed in issued Mehra patents and pending Mehra patent applications.

Depending upon the selected physical solvent and on the economics of a given facility, it may also be necessary to provide a solvent recovery system. Refrigeration, adsorption, and/or a sponge oil system may be utilized.

As defined in pages 102-104 of "Petroleum Refinery Engineering," by W. L. Nelson, second edition, McGraw-Hill Book Co., Inc., New York, 1941, the UOP characterization factor, K, is useful in cataloging crude oils and is even more valuable for defining the degree of paraffinicity of individual fractions. It has also been useful in correlating many properties, such as hydrogen content, aniline point, thermal expansion, viscosity index, and latent heat. It should be noted that if the values of any two of these properties are known, the values of the other properties can be determined. This UOP "K" characterization factor may also be described as an index of the chemical character of pure hydrocarbons and petroleum fractions. The characterization factor of a hydrocarbon is defined as the cube root of these absolute average boiling point in degrees R (°F.+460°) divided by its specific gravity (60° F./60° F.); i.e., the characterization factor equals:

$$K = \frac{\sqrt[3]{T_B}}{s}$$

where
$T_B$ = average boiling point, °R
s = specific gravity at 60° F.

As useful as this characterization factor is, however, it should be borne in mind that it is only an approximate index of the chemical nature of hydrocarbons, as indicated by its variation with boiling point, both for members of a homologous series and for petroleum fractions.

DESCRIPTION OF THE PREFERRED EMBODIMENTS

It should be understood that pipelines are in fact being designated when streams are identified hereinafter and that streams are intended, if not stated, when materials are mentioned. Moreover, flow-control valves, temperature regulatory devices, pumps, and the like are to be understood as installed and operating in conventional relationships to the major items of equipment which are shown in the drawings and discussed hereinafter with reference to the continuously operating process of this invention. All of these valves, devices, and pumps, as well as heat exchangers, accumulators, condensers, and the like, are included in the term, "auxiliary equipment". The term, "absorber", is conventionally employed for a gas/solvent absorbing apparatus, but when it is utilized in the process of this invention with a physical solvent, it is considered to be an "extractor".

In order to demonstrate the performance of various physical solvents for the recovery of ethane from natural gas, several parameters related to the methane-ethane system at 700 psia and −20° F. are summarized in Table II. The inlet gas contains 90 mol % $C_1$ and 10 mol % $C_2$. These conditions of pressure, temperature and composition represent one of the many commercial applications and are selected only for demonstration of this invention. This invention is not to be construed as limited to these conditions.

As can be noted, the selectivity of mesitylene (120 MW), as defined by its KC1/KC2 alpha, of 7.97 is greater than the comparable selectivity of 6.47 for a 120 MW paraffinic solvent. However, the paraffinic solvent requires only 25 gpm circulation when compared to 29 gpm circulation for the mesitylene solvent, i.e., a savings of 15.5% in operating costs. This is primarily due to improved solubility of ethane in the paraffinic solvent (3.13) versus mesitylene (2.71) even though the selectivity of the paraffinic solvent is about 23.2% less than that of the mesitylene solvent.

Figure 1:
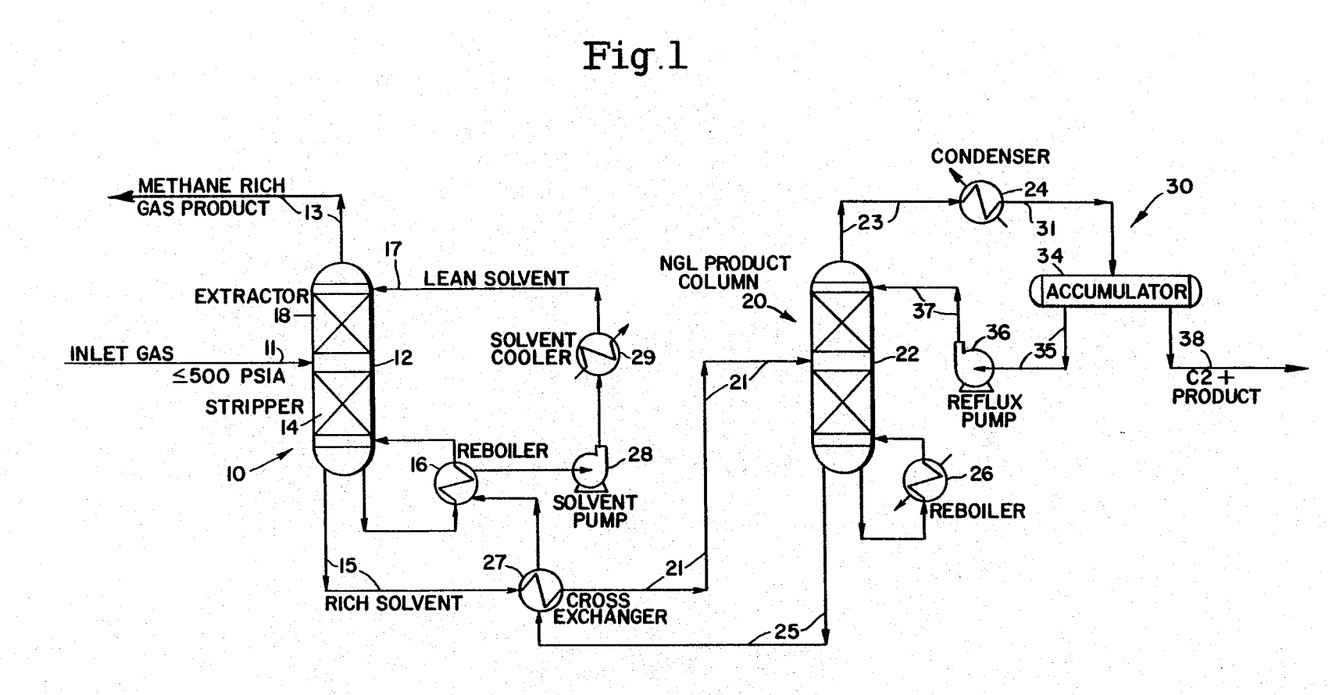
FIG. 1 is a schematic flow sheet for contacting a hydrocarbon gas at any pressure up to 500 psia with a lean physical solvent to produce a $C_2$+hydrocarbons product and a methane-rich gas product.

FIG. 1 illustrates the Extractive-Stripping configuration of the Mehra process for processing natural gas streams at or below 500 psia inlet pressure. In this arrangement, the natural gas enters the extractor-stripper column at the middle. The gas flows upwards and contacts the lean physical solvent flowing downwards over mass transfer surfaces. The solvent, which is rich in hydrocarbons below its feed location, is stripped by the vapor generated through the reboiler or any side reboilers installed in the stripping section of the extractor-stripper column. The rich solvent leaving the bottom of the extractor-stripper column meets the desired specification of the lighter component content in the product.

The rich solvent is heated by the hot lean solvent in the cross-exchanger before entering the NGL product column. In this column, the dissolved hydrocarbons are fractionated out of the solvent and leave overhead as $C_2+$ product. The column overhead is refluxed to minimize solvent losses. The product column is operated at the bottom so that the lean solvent leaving the column meets the hydrocarbon content desired at the top of the extractor-stripper column.

The lean solvent is cooled by exchanging heat through reboilers and cross-exchangers before final cooling in the solvent cooler to the desired temperature for the extraction step.

FIG. 1 shows a process for contacting a hydrocarbon gas stream containing methane and $C_2+$ hydrocarbon components, such as natural gas, at no more than 500 psia with regenerated solvent to produce an off-gas stream of methane-rich gas product and a $C_2+$ hydrocarbons product stream. The inlet gas stream in line 11 enters the midsection of extractor stripper column 12 of unit 10 which is equipped with a reboiler 16 and therein flows countercurrently to a stream of lean solvent from line 17. Column 12 also includes an extractor zone and a stripper zone. An overhead stream in pipeline 13 leaves the process as a methane-rich gas product. A rich solvent, as the bottoms stream, passes through line 15 through cross exchanger 27 and pipeline 21 to enter the midsection of NGL product column 22 of a distillation unit 20.

Column 22 has a reboiler 26 and a reflux apparatus 30. Overhead gases pass through line 23, condenser 24, and line 31 to enter accumulator 34 from which the $C_2+$ hydrocarbons product is withdrawn through line 38. Reflux passes through line 35, reflux pump 36, and line 37 to enter the top of column 22. The bottoms stream of lean-and-dry regenerated solvent passes through line 25, cross exchanger 27, reboiler 16, solvent pump 28, solvent cooler 29, and pipeline 17 to enter the top of column 12.

Figure 2:
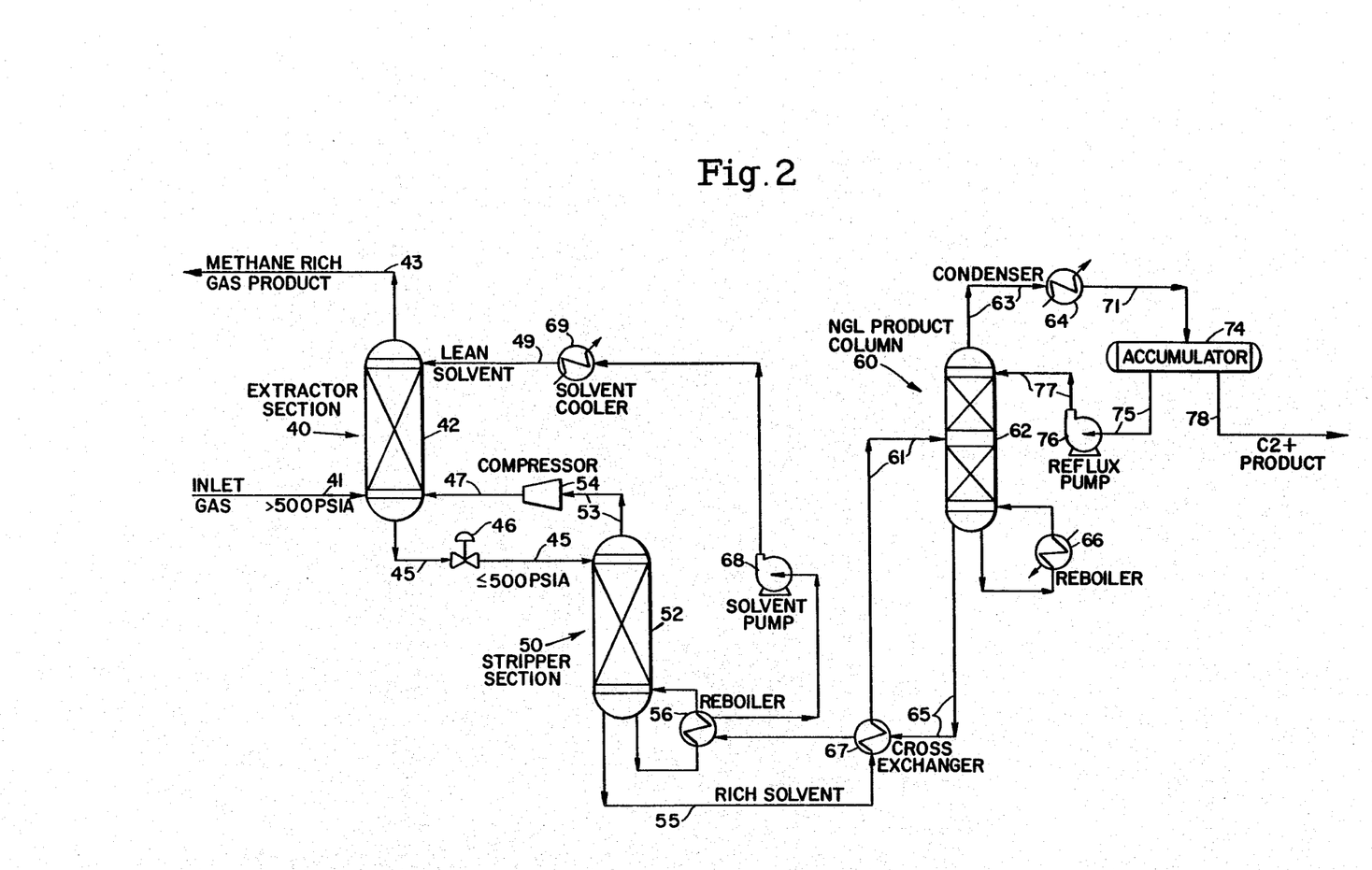
FIG. 2 is a schematic flow sheet for contacting a hydrocarbon gas at a pressure greater than 500 psia with a lean physical solvent to produce a methane-rich gas product as overhead and a $C_2$+hydrocarbons gas product from the rich bottoms solvent after stripping by heating at a pressure of no more than 500 psia, the overhead gas from the stripping operation being recycled to the extractor column.

FIG. 2 depicts the equipment arrangement for the Extractive-Stripping configuration of the Mehra process which is generally used when the natural gas is available at a pressure higher than approximately 500 psia. The primary difference is that the stripping section of the extractor-stripper column operates at lower than approximately 500 psia. This is necessary to avoid operating the stripping section of the column near the system critical pressure as evidenced by the difference between liquid and vapor density less than 20 lbs/cuft. The overhead from the stripping section is compressed and recycled to the bottom of the extraction section. All other parameters are similar to the arrangement in FIG. 1 above.

In FIG. 2, a natural gas stream at a pressure greater than 500 psia is fed by line 41 to extractor column 42 of extractor section 40 and flows countercurrently to a stream of lean solvent which enters the top of column 42 through line 49. A methane-rich gas product leaves through line 43 as the overhead stream, and a bottom stream of rich solvent passes through line 45 to a strip-

TABLE II

PHYSICAL SOLVENT PERFORMANCE
METHANE-ETHANE SYSTEM

BASIS: 1000 LB-MOL/HR FEED CONTAINING 90% C1 AND 10% C2
25% RECOVERY OF ETHANE IN SOLVENT @ 700 PSIA & −20° F.
STP = 14.696 psia @ 60° F.

| TYPE | MW | SOLVENT GAL/MIN STP | C2 SCF/GAL | ALPHA C1/C2 | PREF. FACTOR | S/F RATIO GAL/SCF |
|---|---|---|---|---|---|---|
| Parafinic | 75 | 15 | 5.25 | 6.19 | 32.51 | 0.0024 |
| Parafinic | 85 | 17 | 4.75 | 6.28 | 29.81 | 0.0026 |
| Parafinic | 100 | 20 | 3.98 | 6.44 | 25.60 | 0.0031 |
| Parafinic | 110 | 22 | 3.52 | 6.47 | 22.78 | 0.0036 |
| Parafinic | 120 | 25 | 3.13 | 6.47 | 20.24 | 0.0040 |
| Parafinic | 130 | 28 | 2.81 | 6.42 | 18.01 | 0.0045 |
| Parafinic | 140 | 31 | 2.53 | 6.39 | 16.18 | 0.0049 |
| Naphthenic | 75 | 16 | 4.94 | 7.51 | 37.14 | 0.0025 |
| Naphthenic | 85 | 18 | 4.35 | 7.58 | 32.99 | 0.0029 |
| Naphthenic | 110 | 24 | 3.28 | 7.43 | 24.35 | 0.0038 |
| Naphthenic | 130 | 29 | 2.71 | 7.43 | 20.14 | 0.0046 |
| Benzene | 78 | 24 | 3.27 | 8.69 | 28.43 | 0.0038 |
| Toluene | 92 | 26 | 3.02 | 8.47 | 25.55 | 0.0041 |
| Ethylbenzene | 106 | 24 | 3.26 | 8.00 | 26.07 | 0.0038 |
| m-Xylene | 106 | 25 | 3.20 | 8.03 | 25.72 | 0.0039 |
| Mesitylene | 120 | 29 | 2.71 | 7.97 | 21.59 | 0.0046 | per column 52 of stripper section 50 which is equipped with a reboiler 56. The pressure in column 52 is controlled by using valve 46. The rich solvent is separated into (a) an overhead stream of recycled gases in line 53 which is compressed in recycle compressor 54 and returned to extractor column 42 in line 47 and (b) a bottom stream of partially stripped solvent which is fed through line 55, cross exchanger 67, and line 61 to column 62 of NGL product unit 60 which is equipped with a reboiler 66 and a a reflux apparatus 70. In column 62, rich solvent stream 55 is separated into an overhead stream 63 which is condensed in condensor 64 and passes through line 71 to accumulator 74. A $C_2$+hydrocarbons product is removed from accumulator 74 through line 78. Reflux from accumulator 74 moves through line 75, pump 76, and line 77 to return to the top of column 62. The bottoms stream of lean-and-dry solvent, which has been regenerated, passes through line 65, cross exchanger 67, reboiler 56, solvent pump 68, and solvent cooler 69 into line 49 and the top of column 42.

Figure 3:
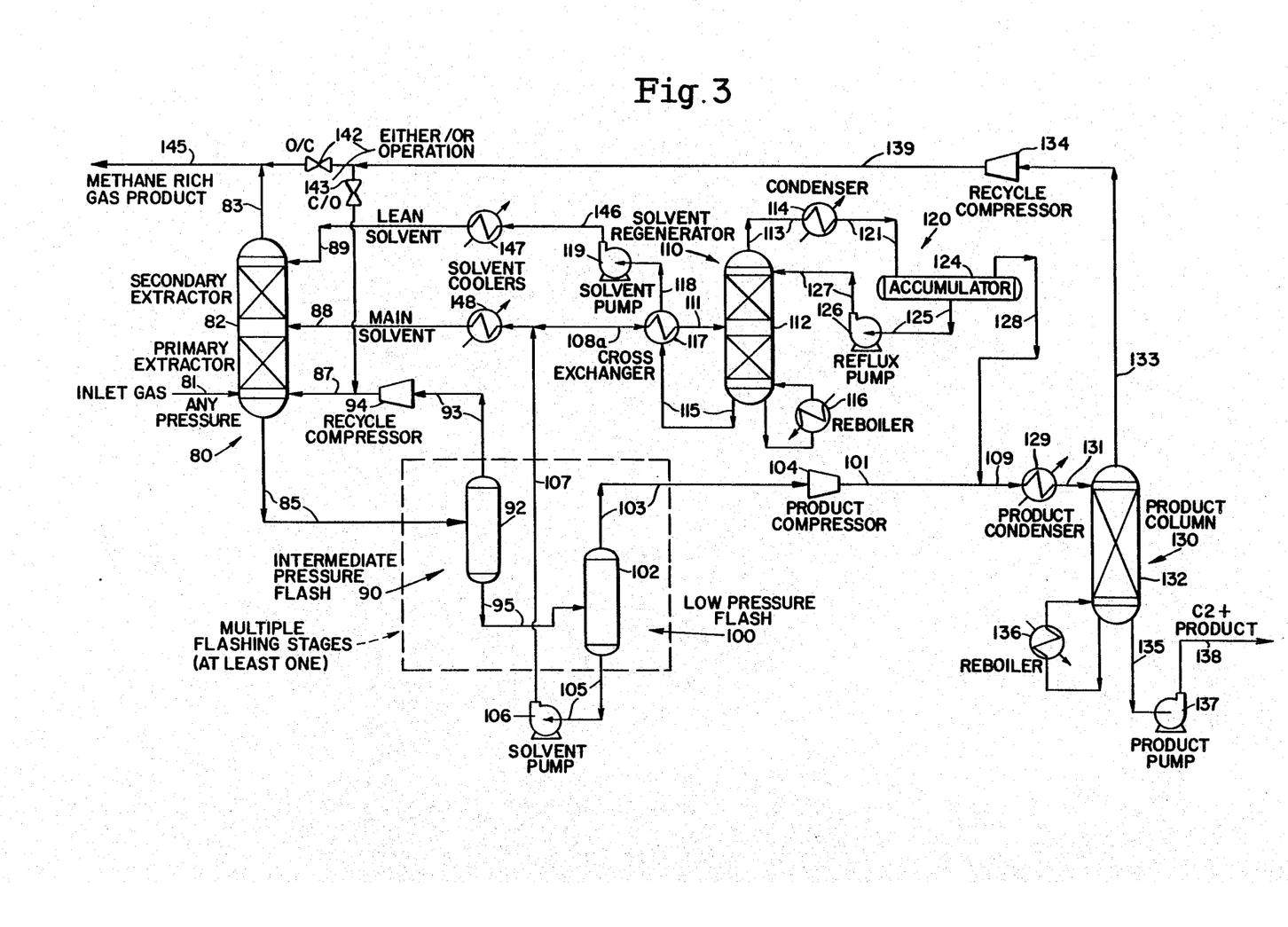
FIG. 3 is another schematic flow sheet for contacting a hydrocarbon gas at any pressure within an extractor column with a main stream of stripped solvent entering the midsection of the column and with a cleanup stream of lean-and-dry solvent entering the top of the column to produce a methane-rich gas product as overhead and a $C_2$+hydrocarbons liquids product from the rich solvent bottoms stream after multiple flashing stages, condensation, and demethanizing, the stripped solvent being split into the main solvent stream and a slipstream which is regenerated in a regenerator column to produce stripped gases as its overhead stream, these gases being added to the methane-rich gas product.

The equipment configuration for processing natural gases at any available pressure by the Extractive-Flashing arrangement is shown in FIG. 3. The slipstream regeneration concept is utilized to minimize the energy consumption and capital expenditure and maximize product purity and recovery.

In this arrangement, the natural gas enters the bottom of the extractor column where the bulk removal of hydrocarbons occurs in the primary extractor section of the column. The final recovery of lighter hydrocarbons such as ethane is accomplished by the contact with the lean solvent entering the top of the secondary extractor section of the column.

The rich solvent leaving the bottom of the extraction column is flashed through multiple flashing stages consisting of at least one flashing stage. If there is more than one flashing stage incorporated, as shown in FIG. 3, the overhead from the initial flashing stage is compressed and recycled to the extraction column or to the inlet feed. The solvent from the first flash is further flashed to separate the extracted hydrocarbons from the solvent. The separated vapors are compressed, cooled, and condensed before stabilization in the product column. Any undesirable gases such as methane are stripped out of the condensed liquids before forming the $C_2$+product. The stripped vapors can either be recycled to the extraction column or passed on directly to the methane-rich gas product.

The solvent from the final flashing stage is split into main and slip solvent streams. The main solvent stream is pumped and cooled before entering the extraction column at the top of the primary extractor section. The slipstream of this partially regenerated solvent is fractionated in the solvent regenerator where any remaining hydrocarbons are separated overhead to flow to the product column. The regenerated solvent forms the lean solvent to the top of the secondary extractor section of the extraction column. After heat exchange, this regenerated solvent flows downwards in the extractor column to join the main solvent stream for further extraction of hydrocarbons in the primary extractor section.

FIG. 3 illustrates a process for obtaining a methane-rich gas product and a $C_2$+hydrocarbons product from a natural gas stream at any pressure by extraction with a selected physical solvent. The natural gas stream in pipeline 81 enters the midsection of a column 82 of extractor unit 80. Column 82 has a a primary extractor section and a secondary extractor section and receives at its top a slipstream of regenerated solvent through line 89, a main solvent stream through line 88, and a recycle gas stream through line 87. An overhead stream of gases leaves column 82 through line 83.

A bottom stream of rich solvent in line 85 enters an intermediate flash column 92 of intermediate pressure flash unit 90 and is split into: (a) an overhead stream of methane-rich gas in line 93 which is raised in pressure in recycle compressor 94 and fed through line 87 to column 82 and (b) a rich solvent bottoms stream which passes through line 95 to low pressure flash unit 100 where it is fed into column 102. It is therein separated into an overhead gas stream in line 103, which is compressed in compressor 104 and fed to line 101, and a bottoms stream which passes through line 105, solvent pump 106 and line 107 before being split into a main solvent stream in line 108 and a slipstream in line 108a.

The main solvent stream is cooled by solvent cooler 148 and fed through line 88 to the midsection of extractor column 82. The slipstream in line 108a passes through cross exchanger 117 and feed line 111 to a regenerator column 112 of solvent regenerator unit 110. Column 112 is equipped with a reboiler 116 and a reflux apparatus 120. The overhead stream from column 112 leaves through line 113, passes through condenser 114 and line 121 and is stored in accumulator 124.

Gases from accumulator 124 leave through line 128 to join the flashed gases in line 101. The resultant gas mixture in line 109 is cooled by product condenser 129 to form a condensate which is fed to the top of product column 132 of product unit 130 through line 131. Column 132 has a reboiler 136. Bottoms leave through line 135 and are forced through line 138 by pump 137.

Returning to accumulator 124, a reflux stream in line 125 is moved by pump 126 through line 127 to the top of column 112. The regenerated solvent, as the bottoms stream of column 112, leaves through line 115, passes through cross exchanger 117 and line 118, is pumped by solvent pump 119 through line 146 and solvent cooler 147 to enter column 82 through pipeline 89.

Returning to column 132, an overhead stream of gases in line 133 is raised in pressure by recycle compressor 134 and flows through line 139 to join overhead stream 83. The combined gases leave the process through take-off line 145 as the methane-rich gas product. However, a side delivery line 144 is connected to line 141. Alternate flow through lines 141, 144 is controlled by open/close valves 142, 143 for either/or operation.

The continuous process of this invention for separating the $C_2$+components of a hydrocarbon gas stream from the methane component thereof comprises the following steps:

A. countercurrently contacting the hydrocarbon gas stream with a physical solvent selected from the group consisting of:
  (1) paraffinic solvents having molecular weights ranging from 75 to 140 and UOP characterization factors ranging from 12.0 to 13.5, the factors being independent of the aromatic content of the paraffinic solvents,
  (2) naphthenic solvents having molecular weights ranging from 75 to 130 and UOP characterization factors ranging from 10.5 to 12.0, these factors being independent of the aromatic content of the naphthenic solvents, and (3) benzene and toluene, to produce an overhead stream which is rich in the methane component and a rich solvent bottoms stream; and B. recovering the $C_2+$ hydrocarbons product and the lean physical solvent from the rich solvent bottoms stream and recycling the recovered lean solvent stream to the contacting of said Step A.

Because it will be readily apparent to those skilled in the art of treating hydrocarbon gases containing components needing to be separated and recovered that innumerable variations, modifications, applications, and extensions of the examples and principles hereinbefore set forth can be made without departing from the spirit and the scope of the invention, what is hereby defined as such scope and is desired to be protected should be measured, and the invention should be limited, only by the following claims.

What is claimed is:

1. In a process for separating a $C_2+$ hydrocarbons product and a methane gas product from a natural gas stream with a physical solvent, comprising the following steps:
   A. contacting said hydrocarbon gas stream with said physical solvent to produce an overhead gas stream of said methane and a rich solvent bottoms stream,
   B. regenerating said solvent bottoms stream to produce an overhead stream of said $C_2+$ hydrocarbons product and a regenerated solvent bottoms stream, and
   C. recycling said regenerated solvent stream to said Step A,
   the improvement comprising said contacting of said Step A, at a pressure no more than approximately 500 psia and at a pressure under which the difference between liquid and vapor density is at least 20 lbs/cubic foot, with said physical solvent selected from the group consisting of
   1. paraffinic solvents having molecular weights ranging from 75 to 140 and UOP characterization factors ranging from 12.0 to 13.5, said factors being independent of the aromatic content of said paraffinic solvents;
   2. naphthenic solvents having molecular weights ranging from 75 to 130 and UOP characterization factors ranging from 10.5 to 12.0, said factors being independent of the aromatic content of said naphthenic solvents; and
   3. benzene and toluene.

2. The improved process of claim 1, wherein said contacting of said Step A occurs within an extractor-stripper column having a reboiler.

3. The improved process of claim 2, wherein said regenerated solvent stream is cross exchanged with said rich solvent bottoms stream from said Step A, cooled, and fed to the top of said extractor-stripper column.

4. The improved process of claim 1, wherein said extractor-stripper column is divided into two columns at different pressures, one said column, which receives said natural gas stream, being at a pressure greater than 500 psia and the other said column being at a pressure no more than 500 psia, the overhead from said second column being compressed and fed to the bottom of said gas-receiving column.

5. A continuous process for separating components of a hydrocarbon gas stream, said components being selected from the group consisting of methane, ethane, higher saturated hydrocarbons, and mixtures thereof, by the following steps:
A. countercurrently contacting said hydrocarbon gas stream with a physical solvent selected from the group consisting of:
   (1) paraffinic solvents having molecular weights ranging from 75 to 140 and UOP characterization factors ranging from 12.0 to 13.5, said factors being independent of the aromatic content of said paraffinic solvents,
   (2) naphthenic solvents having molecular weights ranging from 75 to 130 and UOP characterization factors ranging from 10.5 to 12.0, said factors being independent of the aromatic content of said naphthenic solvents, and
   (3) benzene and toluene, to produce an overhead stream which is rich in said methane and a rich solvent bottoms stream; and
B. recovering said lean physical solvent and said $C_2+$ hydrocarbon product from said rich solvent bottoms stream and recycling said recovered lean solvent stream to said contacting of said Step A,
wherein said recovered lean solvent stream is recovered by flashing thereof and is split into a main solvent stream which is fed to said contacting of said Step A and a slipstream which is heated to form a regenerated solvent stream which is fed sustantially above said feeding of said main solvent stream to said contacting of said Step A.

* * * * *